(12) United States Patent
Strayer

(10) Patent No.: US 6,255,452 B1
(45) Date of Patent: Jul. 3, 2001

(54) EPIDERMAL GROWTH FACTOR INHIBITOR

(75) Inventor: David S. Strayer, Newtown Square, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 08/530,340

(22) PCT Filed: Apr. 4, 1994

(86) PCT No.: PCT/US94/03675

§ 371 Date: Dec. 22, 1995

§ 102(e) Date: Dec. 22, 1995

(87) PCT Pub. No.: WO94/22901

PCT Pub. Date: Oct. 13, 1994

Related U.S. Application Data

(63) Continuation-in-part of application No. 08/041,774, filed on Apr. 2, 1993, now Pat. No. 5,550,114.

(51) Int. Cl.[7] .............. C07K 7/06; C07K 7/08; C07K 14/00
(52) U.S. Cl. .............................. 530/324; 530/327
(58) Field of Search .................. 530/324, 325, 530/350; 514/2; 536/23.1, 235, 327

(56) References Cited

U.S. PATENT DOCUMENTS

| | | | |
|---|---|---|---|
| 4,230,727 | 10/1980 | Nuss et al. | 514/641 |
| 4,289,690 | 9/1981 | Peshea et al. | 530/351 |
| 4,462,986 | 7/1984 | Smith | 424/85.5 |
| 4,569,935 | 2/1986 | Rosenberg et al. | 514/254.07 |
| 4,606,917 | 8/1986 | Eppstein | 424/85.6 |
| 4,929,442 | 5/1990 | Powell | 424/85.2 |
| 4,997,929 | 3/1991 | Collins et al. | 435/365.1 |
| 5,126,323 | 6/1992 | Roger et al. | 514/12 |
| 5,216,176 | 6/1993 | Heindel et al. | 549/280 |
| 5,242,921 | 9/1993 | Milstone et al. | 514/249 |
| 5,473,050 | * 12/1995 | Strand | 530/363 |

OTHER PUBLICATIONS

Brown et al., Nucleic Acids Res., vol. 17, No. 24, p. 10495, 1989*
Rodeck et al., J. Cell. Biochem, vol. 44, pp. 69–79, 1990.*
Strayer et al., Am. J. of Pathol., vol. 142, No. 4, Apr. 1993, pp. 1141–1153.*

Coleman, et al., *Dev. Biol.* (1988) 127:304–315;.
Downward, et al., *Nature* (1984) 311:483–485;.
Drivas, et al., *Mol. Cell. Biol.* (1990) 10:1793–1798;.
Elizalde, et al., *Cancer Invest.* (1990) 8:365–374;.
Ennis, et al., *Molec. Endocrinol.* (1989) 3:1830–1838;.
Eppstein, et al., *J. Cell. Physiol.* (1989) 141:420–430;.
Greenfield, et al., *EMBO J.* (1989) 8:4115–4123;.
Hori, et al., *J. Cell. Physiol.* (1989) 141:275–280;.
Imamoto, et al., *Carcinogenesis* (1990) 11:1543–1549;.
Laurence, et al., *Tumor Biol.* (1990) 11:229–261;.
Matsudaira, P., *J. Biol. Chem.* (1987) 261:10035–10038;.
Matsunami, et al., *FESB Letters* (1980) 264:105–108;.
Murthy, et al., *Biochem. Biophys. Res. Comm.* (1990) 172:471–476;.
Nickoloff, et al., *J. Invest. Dermatol.* (1989) 93:799–803;.
Pearson, et al., *Proc. Natl. Acad. Sci.* (1988) 85:2444–2448;.
Rodeck, et al., *J. Cell. Biochem.* (1990) 44:69–79;.
Sofer, et al., *BioTechniques* (Nov./Dec. 1983) 198–203;.
Strayer, et al., *J. Immunol.* (1983) 130:399–404;.
Strayer, et al., *Am. J. Pathol.* (1987) 128:203–209;.
Stroonbant, et al., *Cell* (1985) 42:383–393;.
Taub. et al., *Proc. Natl. Acad. Sci.* (1990) 87:4002–4006;.
Towbin, et al. *Proc. Natl. Acad. Sci.* (1979) 76:5350–4354; and.
Twardzik, et al., *Proc. Natl. Acad. Sci.* (1985) 83:5300–5304.
Ahn, et al., *J. Biol. Chem.* (1990) 265:11487–11494;.
Ahn, et al., *J. Biol. Chem.* (1990) 265:11495–11501;.
Bischoff, et al., *Nature* (1991) 354:80–82;.

* cited by examiner

Primary Examiner—David Guzo
(74) Attorney, Agent, or Firm—ReedSmith LLP; William J. McNichol, Jr.; Nanda P. B. A. Kumar

(57) ABSTRACT

A protein which is capable of inhibiting epidermal growth factor-induced cellular proliferation is disclosed, as well as a method of obtaining it from a host cell, and a method of obtaining the same in purified form. Therapeutic uses of, and pharmaceutical compositions containing EGFI, TC4 and CDC25 are also described. In addition, the use of EGFI-related gene therapy is described.

4 Claims, 4 Drawing Sheets

SEQUENCE LISTING

<160> NUMBER OF SEQ ID NOS: 7

<210> SEQ ID NO: 1
<211> LENGTH: 11
<212> TYPE: PRT
<213> ORGANISM: Artificial Sequence
<220> FEATURE:

```
<223> OTHER INFORMATION: Description of Artificial Sequence: An
      epidermal growth factor inhibitor peptide

<400> SEQUENCE: 1

His Leu Thr Gly Glu Phe Glu Lys Lys Thr Ser
  1               5                  10

<210> SEQ ID NO: 2
<211> LENGTH: 37
<212> TYPE: PRT
<213> ORGANISM: Artificial Sequence
<220> FEATURE:
<223> OTHER INFORMATION: Description of Artificial Sequence: An
      epidermal growth factor inhibitor peptide

<400> SEQUENCE: 2

Lys Leu Ile Gly Asp Pro Asn Leu Glu Phe Val Ala Met Pro Ala Leu
  1               5                  10                  15

Ala Pro Pro Glu Val Val Met Asp Pro Ala Leu Ala Ala Gln Tyr Glu
                 20                  25                  30

His Asp Leu Glu Val
             35

<210> SEQ ID NO: 3
<211> LENGTH: 14
<212> TYPE: PRT
<213> ORGANISM: Artificial Sequence
<220> FEATURE:
<223> OTHER INFORMATION: Description of Artificial Sequence: An
      epidermal growth factor inhibitor peptide

<400> SEQUENCE: 3

Leu Met Asp Gln Asn Leu Lys Ala Ala Leu Asn Ala Glu Gly
  1               5                  10

<210> SEQ ID NO: 4
<211> LENGTH: 190
<212> TYPE: PRT
<213> ORGANISM: Artificial Sequence
<220> FEATURE:
<223> OTHER INFORMATION: Description of Artificial Sequence: p21 ras
      protein

<400> SEQUENCE: 4

Met Thr Glu Tyr Lys Leu Val Val Val Gly Ala Gly Gly Val Gly Lys
  1               5                  10                  15

Ser Ala Leu Thr Ile Gly Leu Ile Gln Asn His Phe Val Asp Glu Tyr
                 20                  25                  30

Asp Pro Thr Ile Glu Asp Ser Tyr Arg Lys Gln Val Val Ile Asp Gly
             35                  40                  45

Glu Thr Cys Leu Leu Asp Ile Leu Asp Thr Ala Gly Gln Glu Glu Tyr
 50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His Gln Tyr
                 85                  90                  95

Arg Glu Gln Ile Lys Arg Val Lys Asp Ser Asp Asp Val Pro Met Val
                100                 105                 110

Leu Val Gly Asn Lys Cys Asp Leu Ala Ala Arg Thr Val Glu Ser Arg
            115                 120                 125

Gln Ala Gln Asp Leu Ala Arg Ser Tyr Gly Ile Pro Tyr Ile Glu Thr
130                 135                 140
```

```
Ser Ala Lys Thr Arg Gln Gly Val Glu Asp Ala Phe Tyr Thr Leu Val
145                 150                 155                 160

Arg Glu Ile Arg Ile Gln His Lys Leu Arg Lys Leu Asn Pro Pro Asp
                165                 170                 175

Glu Ser Gly Pro Gly Cys Met Ser Cys Lys Cys Val Leu Ser
            180                 185                 190

<210> SEQ ID NO: 5
<211> LENGTH: 216
<212> TYPE: PRT
<213> ORGANISM: Artificial Sequence
<220> FEATURE:
<223> OTHER INFORMATION: Description of Artificial Sequence: Human
      ras-like protein

<400> SEQUENCE: 5

Met Ala Ala Gln Gly Glu Pro Gln Val Gln Phe Lys Leu Val Leu Val
 1               5                  10                  15

Gly Asp Gly Gly Thr Gly Lys Thr Thr Phe Val Lys Arg His Leu Thr
                20                  25                  30

Gly Glu Phe Glu Lys Lys Tyr Val Ala Thr Leu Gly Val Glu Val His
            35                  40                  45

Pro Leu Val Phe His Thr Asn Arg Gly Pro Ile Lys Phe Val Asn Trp
 50                  55                  60

Asp Thr Ala Gly Gln Glu Lys Phe Gly Gly Leu Arg Asp Gly Tyr Tyr
 65                  70                  75                  80

Ile Gln Ala Gln Cys Ala Ile Ile Met Glu Asp Val Thr Ser Arg Val
                85                  90                  95

Thr Tyr Lys Asn Val Pro Asn Trp His Arg Asp Leu Val Arg Val Cys
                100                 105                 110

Glu Asn Ile Pro Ile Val Leu Cys Gly Asn Lys Val Asp Ile Lys Asp
            115                 120                 125

Arg Lys Val Lys Ala Lys Ile Ser Val Phe His Arg Lys Lys Asn Leu
130                 135                 140

Gln Tyr Tyr Asp Ile Ser Ala Lys Ser Asn Tyr Asn Phe Glu Lys Pro
145                 150                 155                 160

Phe Leu Trp Leu Ala Arg Lys Leu Ile Gly Asp Pro Asn Leu Glu Phe
                165                 170                 175

Val Ala Met Pro Ala Leu Ala Pro Pro Glu Val Val Met Asp Pro Ala
            180                 185                 190

Leu Ala Ala Gln Tyr Glu His Asp Leu Glu Val Ala Gln Thr Thr Ala
            195                 200                 205

Leu Pro Asp Glu Asp Asp Asp Leu
210                 215

<210> SEQ ID NO: 6
<211> LENGTH: 120
<212> TYPE: PRT
<213> ORGANISM: Artificial Sequence
<220> FEATURE:
<223> OTHER INFORMATION: Description of Artificial Sequence: CDC25
      protein

<400> SEQUENCE: 6

Lys Met Phe Leu Lys Glu Asn Arg Leu Asn Phe Thr Lys Tyr Phe Asp
 1               5                  10                  15

Leu Ile Ser Asp Ser Ile Val Phe Thr Gln Leu Gly Cys Arg Leu Met
                20                  25                  30
```

-continued

```
Gln His Glu Ile Lys Ala Lys Ser Cys Ser Lys Glu Ile Lys Lys Ile
     35                  40                  45

Phe Lys Gly Leu Ile Ser Ser Leu Ser Arg Ile Ser Ile Asn Ser His
     50                  55                  60

Leu Tyr Phe Asp Ser Ala Phe His Arg Lys Lys Met Asp Thr Met Asn
 65              70                  75                      80

Asp Lys Asp Asn Asp Asn Gln Glu Asn Asn Cys Ser Arg Thr Glu Gly
                 85                  90                  95

Asp Asp Gly Lys Ile Glu Val Asp Ser Val His Asp Leu Val Ser Val
            100                 105                 110

Pro Leu Ser Gly Lys Arg Asn Val
        115                 120

<210> SEQ ID NO: 7
<211> LENGTH: 10
<212> TYPE: PRT
<213> ORGANISM: Artificial Sequence
<220> FEATURE:
<223> OTHER INFORMATION: Description of Artificial Sequence: An
      epidermal growth factor inhibitor peptide

<400> SEQUENCE: 7

Asp Thr His Lys Ser Glu Ile Ala His Arg
 1               5                  10
```

EPIDERMAL GROWTH FACTOR INHIBITOR

This is the United States national stage of International Application No. PCT/US94/03675, international filing date Apr. 4, 1994, which is a continuation-in-part in-part of U.S. Ser. No. 08/041,774, filed Apr. 2, 1993, now U.S. Pat. No. 5,550,114, the contents of which are hereby incorporated by reference.

BACKGROUND OF THE INVENTION

Throughout this application, various references are referred to within parenthesis. Disclosures of these publications in their entireties are hereby incorporated by reference into this application to more fully describe the state of the art to which this invention pertains. Full bibliographic citation for these references may be found at the end of this application, preceding the sequence listing and the claims.

Rapid cell proliferation, in vivo, is responsible for a wide variety of conditions in mammals, including particularly humans, such as carcinomas, sarcomas, tumors, warts, papillomas, psoriasis and keloid scars. There is a continuing need for control and inhibition of such rapid cell proliferation in mammals, particularly human beings.

A number of growth factors which cause rapid cell proliferation are known. Such growth factors include transforming growth factor (TGF), nerve growth factor (NGF) and epidermal growth factor (EGF).

EGF is known to be a prototype for a family of cytokines which are recognized by Epidermal Growth Factor Receptor (EGFR) and which share general similarities in structure.

The present invention was examined in connection with EGF. However, it is anticipated that the present invention is applicable to cellular proliferation facilitated by any member of the EGF family.

EGF's roles in normal physiology and oncogenesis are not clear (1). However, it is known to target both epithelial and stromal cells and to stimulate epithelial growth (2, 3).

Cell activation in response to EGF is facilitated by a specific receptor that recognizes it. After binding EGF, the external domain of EGFR undergoes conformational changes (4), leading to phosphorylation of EGFR cytoplasmic domain. Cell activation follows.

Several types of inhibitors of EGF activity have been reported. Some such inhibitors are structurally unrelated to EGF or EGFR, such as cyclosporin A, interferon-γ, chrysarobin and TGFβ (5, 6). Prostaglandin and some anti-EGFR monoclonal antibodies and phorbol esters also are known to inhibit stimulation of certain target cells by EGF (6, 7, 8, 9). Several monoclonal anti-EGFR antibodies inhibit EGF-dependent growth of a human breast carcinoma cell line in vitro (10).

EGF-like proteins and peptides have also been used to inhibit growth stimulation of target cells by EGF. Small proteins that compete with EGF for EGFR, and mimic EGF activity on target cells have been identified in two human tumors (11). Engineered mutants of EGF are associated with decreased EGF-stimulated tyrosine kinase activity (12). It has been reported that a synthetic peptide encompassing the third disulfide loop of TGFα inhibits EGFR-related growth of human mammary carcinoma cells, although proliferation stimulated by fibroblasts or platelet derived growth factors was unaltered (13).

Several years ago, there was described a protein that appeared to alter the ability of target cells to respond to EGF. Strayer, D. S. et al., Inhibition of Epidermal Growth Factor-Induced Cellular Proliferation, Am. J. Pathol. 128:203–209 (1987).

Heretofore, production and purification methods for, therapeutic uses of, and useful compositions containing, this protein, referred to herein as EGF inhibitor (EGFI) have not been available.

SUMMARY OF THE INVENTION

This invention provides an epidermal growth factor inhibitor protein capable of inhibiting epidermal growth factor-induced cellular proliferation.

This invention also provides a method of obtaining epidermal growth factor inhibitor from a host cell, comprising:
 a) infecting the host cell with a virus;
 b) disrupting the infected host cell wall;
 c) removing cellular debris;
 d) precipitating with methanol;
 e) removing precipitates; and
 f) collecting supernatant containing epidermal growth factor inhibitor.

This invention also provides a method of obtaining purified epidermal growth factor inhibitor from a sample, comprising:
 a) loading the sample onto a reverse phase HPLC column;
 b) eluting from the reverse phase HPLC column with a gradient which proceeds from about fifty percent methanol in aqueous solution to about ninety percent acetonitrile;
 c) collecting a fraction having epidermal growth factor inhibiting activity;
 d) electrophoresing the fraction in an electrophoresis medium; and
 e) recovering protein having a molecular weight of about 34 kilodaltons from the electrophoresis medium, thereby obtaining purified epidermal growth factor inhibitor from the sample.

This invention also provides a method for treating a cell proliferative condition in a mammalian subject, comprising administering to the subject a therapeutically effective amount of an agent selected from the group consisting of epidermal growth factor inhibitor, TC4, and CDC25.

This invention also provides a pharmaceutical composition, comprising a therapeutically effective amount of an agent selected from the group consisting of epidermal growth factor inhibitor, TC4, and CDC25, and a pharmaceutically acceptable carrier.

This invention also provides a nucleic acid molecule comprising a first segment coding for epidermal growth factor inhibitor.

This invention also provides a vector for gene therapy, comprising:
 a) a nucleic acid molecule having i) a transcription regulatory segment; and ii) a second segment coding for a polypeptide having at least fifty percent homology to a polypeptide selected from the group consisting of: the epidermal growth factor inhibitor protein of this invention; TC4; CDC25; an epidermal growth factor inhibitor fragment; a TC4 fragment; and a CDC25 fragment; under transcriptional control of the transcription regulatory sequence; and
 b) a delivery vehicle for delivering the nucleic acid molecule.

DETAILED DESCRIPTION OF THE INVENTION

Figure 1A:
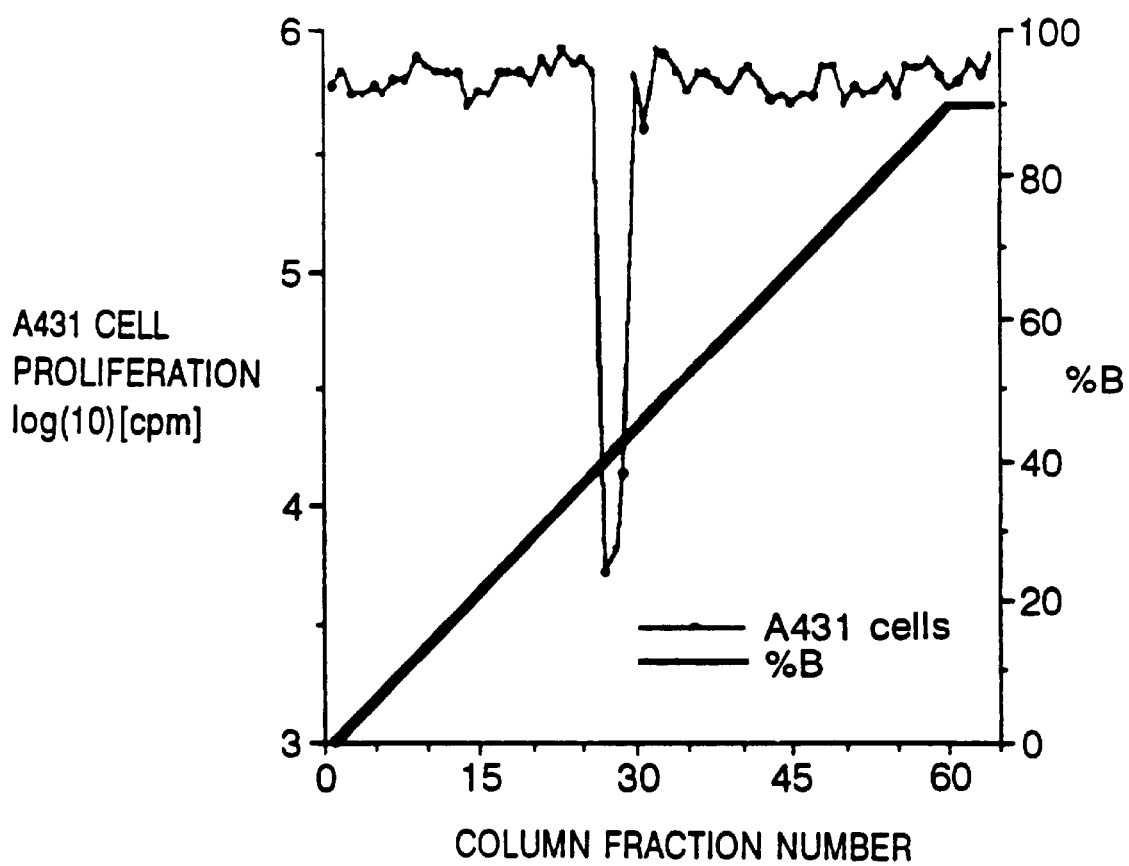
FIG. 1A Inhibition of NRK cell proliferation by column fractions from C18 RP column.

This invention provides an epidermal growth factor inhibitor protein capable of inhibiting epidermal growth factor-induced cellular proliferation.

In an embodiment, the epidermal growth factor inhibitor is produced by a host cell infected with a virus, preferably Malignant Rabbit Fibroma virus. In a preferred embodiment, the host cell is a rabbit kidney cell.

In an embodiment, epidermal growth factor inhibitor comprises a protein having: a first segment having a sequence HLTGEFEKKTS (SEQ ID NO: 1); and a second segment having a sequence KLIGDPNLEFVAMPALAPPE-VVMDPALAAQYEHDLEV (SEQ ID NO: 2), connected to the first segment by at least one peptide bond.

In another embodiment, epidermal growth factor inhibitor comprises a protein which contains a segment having a sequence LMDQNLKAALNAEG (SEQ ID NO: 3).

This invention also provides a method of obtaining epidermal growth factor inhibitor from a host cell, comprising:
a) infecting the host cell with a cancer virus;
b) disrupting the infected host cell wall;
c) removing cellular debris;
d) precipitating with methanol;
e) removing precipitate; and
f) collecting supernatant containing epidermal growth factor inhibitor.

In an embodiment of the method of obtaining epidermal growth factor inhibitor from a host cell, the host cell is RK-13 rabbit kidney cell. In another embodiment, the cancer virus is malignant Rabbit Fibroma Virus.

The cell wall of the infected host cell may be disrupted by techniques well known to those of skill in the art. However, mechanical disrupting is preferred, examples of which include freezing and thawing, including multiple freezing and thawing; and sonicating.

The cellular debris may be removed by any technique within the capability of a person of ordinary skill in the art to which this invention pertains. In a preferred embodiment, the cellular debris is removed by filtering.

In a preferred embodiment, precipitating with methanol is precipitating with a final methanol concentration in solution of about fifty percent. This may be done by adding a roughly equivalent volume of 100% methanol, thereby resulting in a final concentration of methanol in solution of 50%.

Precipitate and supernatant may be separated using techniques known to those of skill in the art. In a preferred embodiment, the precipitate is removed by centrifuging.

This invention also provides a method of obtaining purified epidermal growth factor inhibitor from a sample, comprising:
a) loading the sample onto a reverse phase HPLC column;
b) eluting from the reverse phase HPLC column with a gradient which proceed s from about fifty percent methanol in aqueous solution to about ninety percent acetonitrile;
c) collecting a fraction having epidermal growth factor inhibiting activity;
d) electrophoresing the fraction in an electrophoresis medium; and
e) recovering protein having a molecular weight of about 34 kilodaltons from the electrophoresis medium,
thereby obtaining purified epidermal growth factor inhibitor from the sample. The gradient preferably contains about one tenth of one percent trifluoroacetic acid (0.1% TFA) throughout the elution process.

In a preferred embodiment, step c) comprises:
i) determining a fraction having epidermal growth factor inhibiting activity; and
ii) collecting the fraction having epidermal growth factor inhibiting activity.

In an especially preferred embodiment, a fraction having epidermal growth factor inhibiting activity is determined by contacting an aliquot of the fraction to NRK cells.

The electrophoresis medium is preferably sodium dodecyl sulfate-polyacrylamide gel. In an embodiment, the gel is 10% polyacrylamide in sodium dodecyl sulfate.

The approximately 34 kDa EGFI protein may be recovered from the gel by techniques known to those of skill in the art. Examples of such techniques include electroeluting, especially electroeluting into a dialysis bag, and electrophoresis onto a membrane.

In a specific embodiment, the method of obtaining purified epidermal growth factor inhibitor from a sample comprises the steps of:

passing the protein-containing supernatant through a semi-preparative C18 reverse phase HPLC column, wherein a flow rate of 1 ml/min is maintained as the gradient proceeds from 100% solvent A (50% water: 49.9% methanol: 0.1% trifluoroacetic acid (TFA)) to 90% solvent B (99.9% acetonitrile: 0.1% TFA) in 60 minutes;

analyzing effluent from the C18 column using a diode array detector, scanning from 190 to 310 nm at 5 second intervals;

pooling like fractions from sequential runs;

removing solvents;

redissolving resulting 34 kDa protein in saline;

separating the 34 kDa protein by preparative electrophoresis;

recovering the 34 kDa protein from the electrophoresis gel by electroelution;

and resuspending the 34 kDa protein in saline.

This invention also provides a method for treating a cell proliferative condition in a mammal, comprising administering a therapeutically effective amount of an agent selected from the group consisting of epidermal growth factor inhibitor, TC4, and CDC25.

In an embodiment, this invention provides a method of treating a cell proliferative condition in a mammal, comprising administering to the subject a therapeutically effective amount of a mixture of TC4 and CDC25. Preferably, the concentrations of TCH and CDC25 are approximately equal.

In another embodiment, TC4 is complexed with CDC25, for example by hydrogen bonding or other electrostatic interactions. Alternatively, TC4 may be covalently bonded to CDC25 by one or more covalent bonds, including Cys-Cys disulfide bonds and peptide bonds.

In an embodiment, this invention provides a method for treating a cell proliferative condition in a mammal, such as, a skin condition, or an abnormal proliferation of fibroblasts such as keloids, hypertrophic scars, benign or malignant proliferations of fibroblasts. The method comprises administering at the affected area a therapeutically effective amount of an agent selected from the group consisting of epidermal growth factor inhibitor, TC4, and CDC25.

In another embodiment, this invention provides a method for treating a cell proliferative condition in a mammal, such as a benign or malignant tumor. Such tumors may be located in mucous membranes of the mammal, including the upper respiratory system, nose, nasopharynx, mouth, oropharynx, pharynx, external covering of the eye, lower female genital tract, and anus. Such tumors may include proliferation of epithelial tissue, soft tissue, hematopoietic tissue, or germ cell tissue.

This invention also provides a pharmaceutical composition, comprising a therapeutically effective amount of an agent selected from the group consisting of epidermal growth factor inhibitor, TC4, and CDC25, and a pharmaceutically acceptable carrier.

In an embodiment of the pharmaceutical composition of this invention, the epidermal growth factor inhibitor is a mixture of TC4 and CDC25. In a preferred embodiment, the concentrations of TC4 and CDC25 are approximately equal. In another embodiment, TC4 is complexed with CDC25, for example by hydrogen bonding or other electrostatic interactions. Alternatively, TC4 may be covalently bonded to CDC25 by one or more covalent bonds, including Cys-Cys disulfide bonds and peptide bonds.

Pharmaceutically acceptable carriers are known to those of skill in the art. As examples, the pharmaceutically acceptable carrier may be an aqueous solution or a non-aqueous solution.

In one embodiment, the pharmaceutical composition is in a form suitable for oral ingestion. In another embodiment, the pharmaceutical composition is in a form suitable for topical application. Examples of forms suitable for topical application include a transdermal patch; a salve; an ointment; a cream; a gel; a rinse; a mouthwash; a mist; and an aerosol spray. In another embodiment, the pharmaceutical composition is in a form suitable for application to mucous membranes of a mammal. Examples of forms suitable for application to mucous membranes of a mammal include an ointment; a cream; a gel; a mist; a spray, including a nebulized preparation; and a mouthwash.

This invention also provides a pharmaceutical composition comprising a therapeutically effective amount of an agent selected from the group consisting of epidermal growth factor inhibitor, TC4, and CDC25, together with an agent selected from the group consisting of an anti-viral agent, and an anti-microbial agent, or an anti-neoplastic agent and pharmaceutically acceptable carrier.

This invention also provides a nucleic acid molecule comprising a segment coding for epidermal growth factor inhibitor. The nucleic acid molecule may be DNA, including cDNA, or RNA. In an embodiment, the nucleic acid molecule further comprises a transcription regulatory segment which regulates transcription of the first segment.

This invention also provides a vector for gene therapy, comprising:

a) a nucleic acid molecule having i) a transcription regulatory segment; and ii) a segment coding for a polypeptide having at least fifty percent homology to a polypeptide selected from the group consisting of: the epidermal growth factor inhibitor protein of this invention; TC4; CDC25; an epidermal growth factor inhibitor fragment; a TC4 fragment; and a CDC25 fragment; under transcriptional control of the transcription regulatory sequence; and b) a delivery vehicle for delivering the nucleic acid molecule.

In an embodiment of the vector, the nucleic acid molecule is a DNA molecule. The DNA molecule may be cDNA. Alternatively, it may be a gene. In another embodiment, the nucleic acid molecule is a RNA molecule.

In an embodiment, the nucleic acid molecule is a virus or a modified virus. In a specific embodiment, the virus is selected from the group consisting of: an adenovirus, an adeno-associated virus, a retrovirus, a herpes virus, a pox virus, a polyoma virus, a papilloma virus, a parvovirus, an arbovirus, and a hebdnavirus. In another embodiment, the nucleic acid molecule is a plasmid or a modified plasmid.

In a preferred embodiment, the transcription regulatory segment is a promoter. In an embodiment, the regulatory segment is a specific regulatory segment. In another embodiment, the regulatory segment is a nonspecific regulatory segment.

In a specific embodiment, a segment codes for a polypeptide having at least fifteen percent homology to a polypeptide selected from the group consisting of: the epidermal growth factor inhibitor protein of this invention; TC4; CDC25; an epidermal growth factor inhibitor fragment; a TC4 fragment; and a CDC25 fragment. In a presently preferred embodiment, the second segment codes for a polypeptide selected from the group consisting of: the epidermal growth factor inhibitor protein of this invention; TC4; CDC25; an epidermal growth factor inhibitor fragment; a TC4 fragment; and a CDC25 fragment.

In an embodiment of the vector, the delivery vehicle is a viral envelope. In a specific embodiment, the viral envelope is of an adenovirus, an adeno-associated virus, a retrovirus, a herpes virus, a pox virus, a polyoma virus, a papilloma virus, a parvovirus, an arbovirus or a hebdnavirus.

In an embodiment of the vector, the delivery vehicle is a liposome or a modified liposome. Preferably, the liposome comprises an antibody for targeting cells displaying antigens which bind to the antigen. In an embodiment the liposome comprises a phospholipid. In another embodiment, the liposome comprises a steroid, preferably cholesterol or a derivative thereof.

This invention also provides a pharmaceutical composition comprising the vector- described above and a pharmaceutically acceptable carrier.

This invention also provides a method for treating a cell proliferative condition in a mammal, comprising administering to the subject a therapeutically effective amount of the vector. A person of skill in the art will understand appropriate techniques of administering a vector. Preferred techniques include: injecting, inhaling, applying topically, and ingesting.

This invention will be better understood from the Experimental Details which follow. However, one skilled in the art will readily appreciate that the specific methods and results discussed are merely illustrative of the invention as described more fully in the claims which follow thereafter.

Experimental Details

RK-13 rabbit kidney cells were received from W. A. Tompkins, University of Illinois, Urbana, Ill. NRK cells, clone 49F, were purchased from American Type Culture Collection. A431 squamous carcinoma cells were the kind gift of Dr. Gordon Gill, University of California, San Diego. Techniques for passaging these cells have already be described (14, 25). Where reported, cell viability was determined by trypan blue exclusion.

Malignant rabbit fibroma virus was used. Its preparation, culture and storage are described elsewhere (15).

The assay of the ability of EGFI to inhibit EGF-induced cellular proliferation was described previously. Strayer, D.

S. et al, Inhibition of Epidermal Growth Factor—Induced Cellular Proliferation. 1987 Am. J. Patholo. 128:202–209. In summary, NRK cells were passaged as usual until 1 day before the assay. At that time, they were transferred to Costar 24-well culture dishes in Dulbecco's modified Eagle's Medium (DMEM) with 0.5% Fetal Bovine Cell Serum (FCS). The following day, cells were washed with DMEM without serum and cultured with or without added EGF, EGFI or other supplement for 4–5 days. 24-hour incorporation of $^3$H-thymidine was measured by adding 5 $\mu$Ci $^3$H-thymidine to each 1 cm$^2$ culture well, then harvesting the cells and counting incorporated radionucleotide one day later.

Established protocols used to purify EGF as guides in devising an approach to purifying EGFI (16, 17). Rabbit kidney cell line RK-13 cells were infected with malignant Rabbit Fibroma Virus (MV) at a multiplicity of infection (MOI) of 3.0 in serum-free medium. After 36 hours, medium was removed and the cells washed with saline, then frozen, thawed and sonicated. This lysed cell preparation was filtered and mixed 1:1 with 100% methanol. This step precipitates about 90% of the protein in these preparations. Precipitates were removed by centrifugation.

Each application of the protein-containing sample in 50% methanol to the 1×25 cm semipreparative Supelco C18 reverse phase high pressure liquid chromatography (HPLC) column involved 10 mg total protein. A flow rate of 1 ml/min was maintained as the gradient proceeded from 100% solvent A (50% water: 49.9% methanol: 0.1% trifluoroacetic acid (TFA)) to 90% solvent B (99.9% acetonitrile: 0.1% TFA) in 60 minutes. Effluent from the column was analyzed using a LKB Instruments diode array detector, scanning from 190 to 310 nm at 5 sec. intervals.

Following this gradient, like fractions from sequential runs were pooled, solvents removed and proteins redissolved in saline. These were added to cultures of NRK cells as described, to identify the fractions(s) with EGFI activity.

The fractions showing EGFI activity contained two detectable proteins. They were separated by preparative electrophoresis. Initial work involved separation by agarose gel electrophoresis. However, subsequently, preparative SDS-PAGE was used. Before electrophoresis, proteins were boiled for 8 min. in the presence of 4 mmol/L 2-mercaptoethanol and electrophoresed in gels containing SDS-10% polyacrylamide. Protein was recovered from the individual bands in the gel by electroelution, followed by resuspension in saline. Protein purity was ascertained by size exclusion chromatography using LKB Instruments TSK4000 column.

Sequence Analysis

Preliminary analysis showed EGFI N-terminus to be blocked. Thus, the proteins were purified by SDS-PAGE and transferred to nitrocellulose (18), from which tryptic digestion was performed and these tryptic fragments isolated and sequenced (19).

Sequence information from the purified proteins was compared with protein sequences entered in GenBank using the FastaServe algorithm (20).

Protein Phosphorylation After Exposure to EGF, EGFI

NRK or A431 cells were cultured as usual. One day before the assay, the cells were transferred to Costar 6 well cluster dishes in serum-free medium. On the day of the assay, medium was changed, and cells were grown for 3 hours in normal saline supplemented with glucose and essential amino acids. EGF and/or EGFI were then added, and at various time intervals thereafter, 50 $\mu$Ci $^{32}$PO$_4$. Cells were incubated with radiolabeled phosphate for 30 min., then washed extensively with normal saline and lysed with NS-1% Nonidet (Shell Chemical Corp.). Protein was precipitated by adding equal volumes of 15% trichloroacetic acid (TCA), washed with 10% TCA in water, resuspended in saline and analyzed by SDS-PAGE. Aliquots of protein precipitate were counted in a Beckmann Instruments scintillation counter.

Protein Production

Cells were incubated in 24-well cluster dishes with leucine-free DMEM-0.5% dialyzed fetal bovine serum with or without added EGF (5 ng/ml) or EGFI (50 ng/ml). After various time periods, 10 $\mu$Ci of $^3$H-leucine was added. One hour later, cultures were terminated by washing the adherent cells exhaustively with normal saline, lysing with water-0.1% SDS, and adding an equal amount of 15% TCA. Precipitated proteins were washed in 10% TCA, resuspended in saline, and protein-incorporated radioactivity counted. Parallel cultures were performed to measure viable cell recovery.

In addition, proteins from each culture time and condition were electrophoresed with SDS-PAGE. Gels were dried and autoradiographed.

Glucose and Lactate Determinations

One ml aliquots of culture supernatants from cultures of NRK and A431 cells with or without EGF, EGFI and EGFI were harvested and their glucose (hexokinase technique, Hitachi 717) and lactate (LDH technique, Dupont aca II) measured by automated analyzers.

Purification of EGFI

Figure 1B:
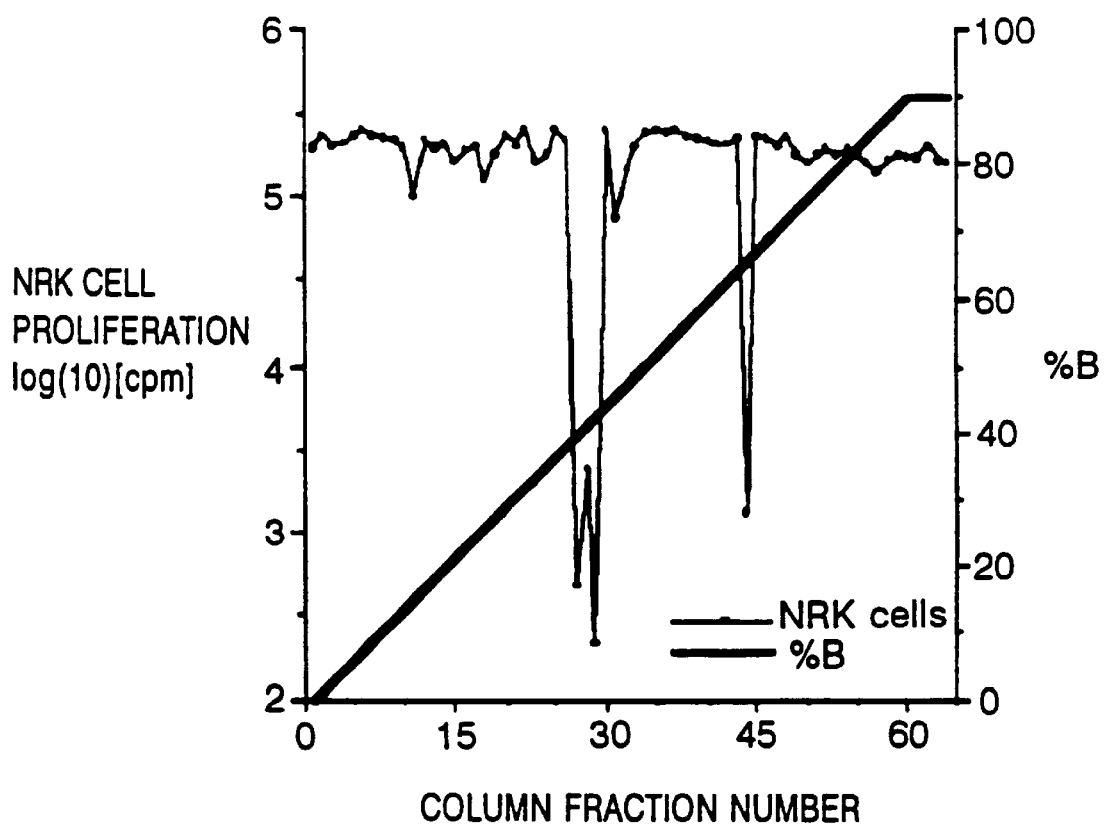
FIG. 1B Inhibition of A431 cell proliferation by column fractions from C18 RP column.

Crude lysates of RK-13 cells that inhibited EGF responses of NRK cells were eluted from an RP-HPLC gradient that went from 50% water-49.9% methanol; 0.1% TFA to 89.9% acetonitrile-5% water-5% methanol-0.1% TFA. Fractions were collected and solvents removed. Proteins were redissolved in normal saline and assayed for their ability to alter proliferation of EGF-response NRK cells and EGFR-bearing A431 cells. As seen in FIGS. 1A and 1B, inhibition of EGF-induced NRK cellular proliferation corresponded to a small number of fractions eluting at about 30% solvent B.

Fractions containing EGF inhibitory activity were pooled and analyzed by SDS-PAGE. They contained two principal proteins: one of approximately 68 kDa ($M_T$) and the other 34 kDa.

These proteins were purified by electroelution from SDS-PAGE gels. Purity of resultant proteins was verified by gel filtration HPLC, analyzing effluent with a scanning diode array detector. Both proteins were found to be pure.

UV-visible absorption spectra (190–310 nm) examined during peak elution were found to be invariant throughout the elution time. As a second protein component would have a different absorption spectrum, inhomogeneity would be appear as difference in UV-visible absorption spectra compared at the beginning and at the end of the eluting peak. This is consistent with 34 kDa EGFI band containing a single polypeptide chain. It is also consistent with a complex of more than one polypeptide chain linked covalently or noncovalently.

Protein Sequence Analysis of the two Components of the RP-HPLC Peak

Following purification by gel electrophoresis an attempt was made to sequence the two components of the reverse phase peak that inhibits NRK cellular responses to EGF. The 68 kDa protein (p68) was sequenced for the following 10 amino acids: DTHKSEIAHR (SEQ ID NO:7). Its sequence exhibited considerable homology to human and bovine preproalbumin sequences.

Attempts to sequence the 34 kDa protein (p34) directly were unsuccessful, indicating a blocked N-terminus. The 34 kDa band was excised from a nitrocellulose filter after SDS-PAGE separation from the larger protein, and digested with trypsin. Tryptic digestion products were eluted from a C18 RPHPLC column and two such fragments were sequenced. These sequences are shown in Table 1 below, which shows comparative amino acids sequences of two tryptic fragments of the 34 kDa EGF inhibitor, $p21^{ras}$ and the updated (March, 1992) sequence for TC4, obtained from GenBank. Residues where the two are identical are denoted by a vertical bar (|), while those where they differ are denoted by an asterisk (*).

As can be seen from Table 1, the residues of two of this protein's tryptic fragments show striking homology to a 24 kDa protein identified originally as a ras-like protein identified as an mRNA in human teratocarcinoma cells (21,22).

cDNA clones, the only protein having a sequence corresponding to the TC4-like sequence which has been clearly identified is rabbit TC4. An EGFI protein distinct from TC4 and CDC25 which contains both TC4-like and CDC25-like sequences has not yet been identified.

Although it is still possible that with continued screening of the cDNA library an EGFI protein that contains both TC4-like and CDC25-like sequences will be uncovered, the most likely explanation is that EGFI is a complex of TC4 and CDC25, or related proteins. Accordingly, in addition to treatment with and pharmaceutical compositions which include EGFI, this invention also provides for methods of treatment utilizing and pharmaceutical compositions which include TC4, CDC25 or CDC25-like proteins, mixtures of TC4 with CDC25 or CDC25-like proteins, as well as com-

TABLE 1

```
p21ras                          MTE YKLVVVGAGG VGKSALTIQL
Human ras-like protein:     MAAQGEPQVQ FKLVLVGDGG TGKTTFVKRH
                                                           |
EGFI                                                       H IQNHFVDEYD PTIEDSYRKQ VVIDGETC-L LDILDTAGQE EYSAMRDQYM
LTGEFEKKYV ATLGVEVHPL VFHTNRGPIK FVNWDTAGQE KFGGLRDGYY
|||||||||* *
LTGEFEKKT- S (SEQ ID No:1)

RTGEGFLCVF AINNTKSFED IHQYREQIKR VKDSDDVPMVLV GNKCDLAART
IQAQCAIIMF DVTSRVTYKN VPNWHRDLVR VCEN--IPIVLC GNKVDIKDRK

VESRQAQ-DLAR SYGIPYIETS AKTRQGVEDA FYTLVREIRI QHKLRKLNPP
VK--AKSIVFHR KKNLQYYDIS AKSNYNFEKP FLWLARKLIG DPNLEFVAMP
                                      ||||  ||||||||||
                                      KLIG  DPNLEFVAMP

DESGPGCMSC KCVLS (SEQ ID NO:4)
ALAPPEVVMD PALAAQYEHD LEVAQTTALP DEDDDL (SEQ ID NO:5)
|||||||||| |||||||||| |||
ALAPPEVVMD PALAAQYEHD LEV (SEQ ID NO:2)
```

Additional protein sequencing yielded a series of sequences that resemble CDC25, a cell cycle control protein. As can be seen from Table 2, one such sequence, LMDQN-LKAALNAEG (SEQ ID NO:3) displays 50% identity with CDC25 in an 8 amino acid residue overlap. Residues where the two are identical are denoted by a vertical bar (|), while those where they differ are denoted by an asterisk (*).

TABLE 2

```
EGFI                                      LMDQNLKAAL
                                          ||****||**
CDC235 KMFLKENRLN FTKYFDLISD SIVFTQLGCR LMGHEIKAKS

NAEG (SEQ ID NO:3)
****
CSKEIKKIFK GLISSLSRIS INSHLYFDSA FHRKKMDTMN DKDNDNQENN

CSRTEGDDGK IEVDSVHDLV SVPLSGKRNV (SEQ ID NO:6)
```

Purification and Identification of cDNA Clones

Degenerate oligonucleotide probes were generated based on the sequences of EGFI fragments which correspond to human ras-like protein. Using these probes, a number of cDNA clones from a rabbit cDNA library were identified and purified. Based on protein sequences derived from these plexes of them in which the two components may be linked covalently or by electrostatic interactions.

Ability of p34 to Inhibit EGF Activity

Figure 2:
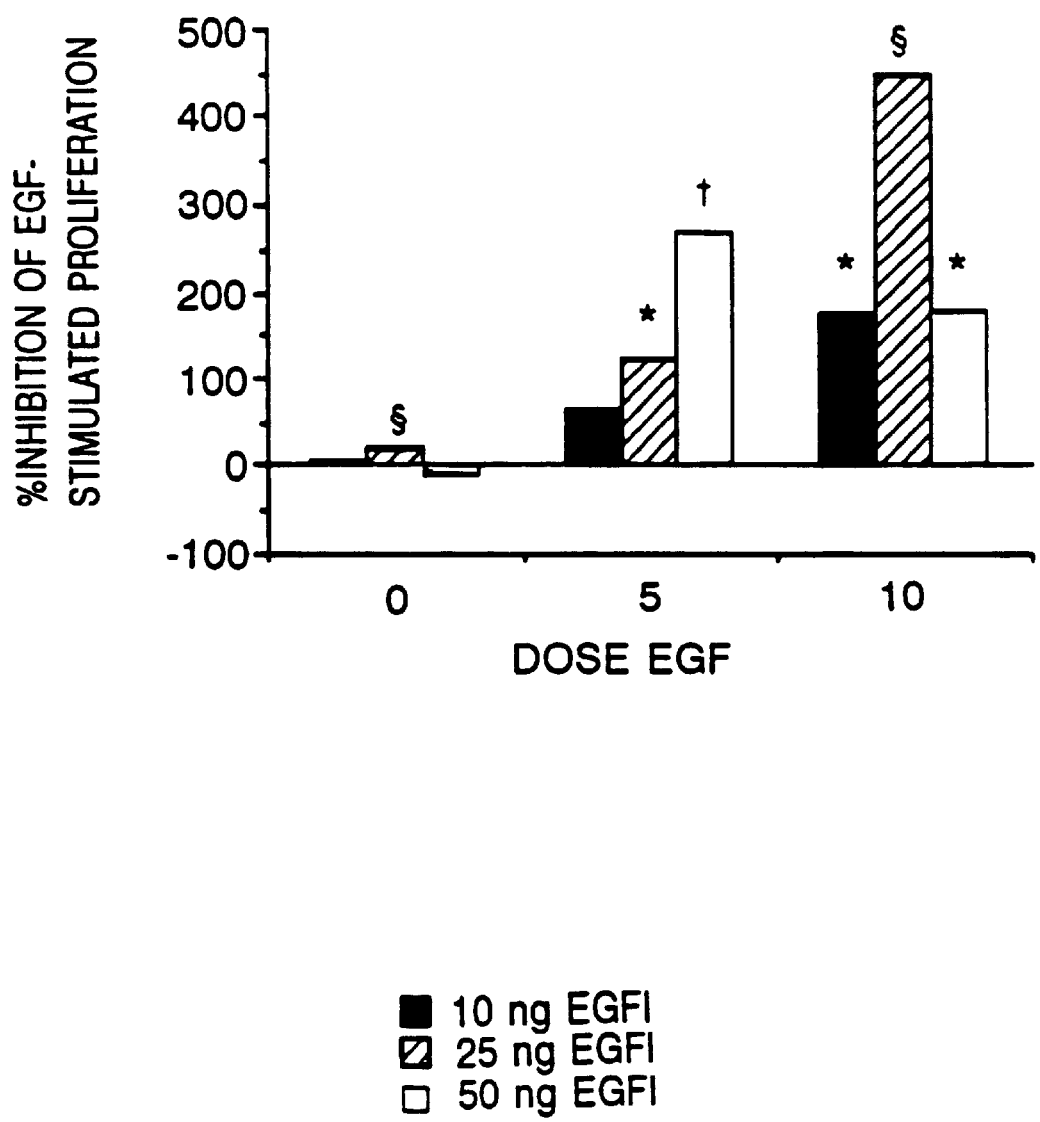
FIG. 2 Inhibition of EGF-stimulated proliferation of NRK cells.

To determine whether p34 altered EGF-induced NRK cellular activation in vitro as an EGF inhibitor, EGF was added in 5 or 10 ng/ml concentrations to cultures of serum-starved NRK cells. Simultaneously, 10, 25, 50 ng/ml p34, purified as above, was added. In a dose dependent fashion, purified p34 completely inhibited EGF-stimulated NRK cell proliferation, as can be seen in FIG. 2.

At 10 and 25 ng/ml p34 also reduced unstimulated NRK proliferation to levels below the those observed without added EGF. Optimal inhibition was seen at approximately 25 ng/ml, depending on EGF concentration. Thus, p34 appears to inhibit EGF-induced cell proliferation (EGFI).

Figure 3:
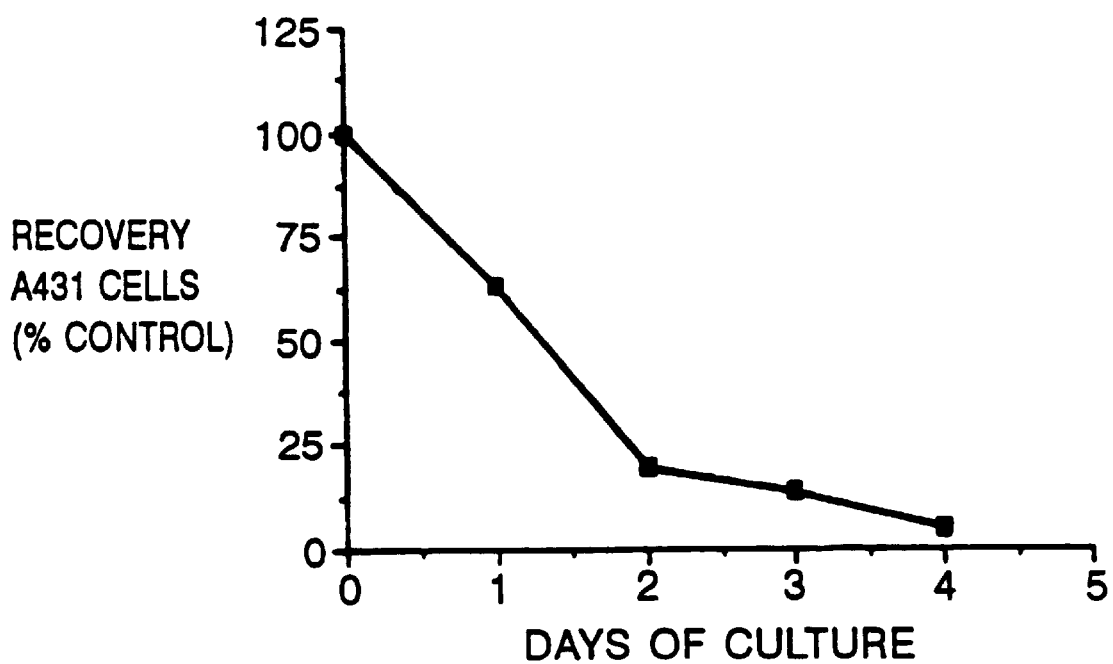
FIG. 3 Recovery of A431 cells cultured with EGFI.

The effects of p34 on A431 cells were even more surprising. 25–50 ng/ml of p34 caused A431 squamous carcinoma cells to lift off tissue culture dishes by 4–5 days of culture. Trypan blue exclusion was used to assess effects of p34 on A431 cell recovery in vitro. By five days after adding p34 very few viable A431 cells were recovered, as shown in FIG. 3.

In contrast, A431 cells cultured without p34 continue to proliferate.

Effects of p34 on Protein Phosphorylations

Phosphorylation of cytoplasmic proteins is an important step in cellular activation following EGF and TGFα interaction with EGFR (23, 24, 25). The effects of p34 on protein phosphorylation in EGF-stimulated and unstimulated NRK and A431 cells were examined. EGF-(5 ng/ml and/or EGFI (50 ng/ml) were added to cells in serum-free and phosphate free medium. $^{32}PO_4$ (50 µCi/ml) was added at various times. Cells were harvested 30 minutes after addition of $^{32}PO_4$ and analyzed by SDS-PAGE and autoradiography. P34 altered protein phosphorylation in both NRK and A431 cells, whether EGF was present or not.

This difference was observed at all times from 0 to 12 hr. after EGF/EGFI addition. The distinctive patterns of alteration induced by EGFI were consistent from one time point to the next and were similar when the phosphorylated proteins from A431 and NRK cells were compared.

When $^{32}PO_4$ incorporation into protein was measured as a function of time after exposure to EGFI and/or EGF, it was discovered that levels of protein phosphorylation in NRK cells increased dramatically between 4 and 20 hours of culture. At all times, NRK cells cultured with EGFI incorporated significantly less $^{32}PO_4$ into protein that did control cells incubated without EGFI.

At all time points after 2 hours of incubation, cells incubated with EGF and EGFI incorporated less $^{32}PO_4$ then did control cells exposed only to EGF.

The effects of EGFI on protein phosphorylation in A431 cells were less consistent than those in NRK cells, although adding EGFI caused substantial differences in incorporated $^{32}PO_4$ at several time points. Generally, A431 cells incubated with EGFI, with or without EGF, phosphorylated less protein than did control A431 cells.

Effects of EGFI on Aspects of Cellular Metabolism

To determine whether exposure to EGFI altered protein production and glucose utilization, EGFI was added to cultures of NRK and A431 cells, with and without EGF, and these parameters were measured at selected times thereafter. Data were corrected for cell number and, in the case of glucose and lactate determinations, total protein.

To measure protein production as a function of EGFI exposure, A431 and NRK cells were incubated in leucine-free medium with or without EGF and/or EGFI. At various times after culture initiation $^3$H-Leu was added to the culture medium and cells harvested one hour later. Both EGF and EGFI stimulated protein production moderately 2 days after culture initiation, but not significantly thereafter. The stimulatory effects of EGF and EGFI were not additive.

Despite increased protein synthesis as a whole, however, we detected no change in the species of proteins produced. $^3$H-Leu-labeled proteins from NRK or A431 cultures were prepared as described above and electrophoresed in SDS-PAGE. After electrophoresis, gels were dried and autoradiographed.

There appears to be little difference in the major species of proteins produced on exposure to EGF and/or EGFI. The time of exposure to these cytokines did not alter the result. Those protein species produced by cells after 2 hours exposure to EGF and/or EGFI did not differ appreciably from those produced after 44 hours exposure.

Lactate production and glucose utilization were measured as well. Though absolute values for these indices differed significantly in EGF and EGFI treated cells compared to control cells, when these values were corrected for cell numbers and total protein content, these indices were found to be equivalent among all groups.

Clinical Uses of Epidermal Growth Factor Inhibitor

The Epidermal Growth Factor Inhibitor of this invention can reasonably be expected to have clinical use in the treatment of animals, particularly mammals, most particularly human beings since it has been shown above that in vitro tests, the presence of Epidermal Growth Factor Inhibitor can markedly decrease or completely inhibit rapid cell proliferation induced by EGF.

The striking results of the in vitro tests described above demonstrate that the Epidermal Growth Factor Inhibitor described herein has utility in the treatment of disorders in animals, particularly humans, caused by EGF-related rapid cell proliferation. Such disorders include psoriasis, keloid scarring, warts, leukoplakia, keratoses, carcinomas, sarcomas and condylomas.

Based on the sequence data described above, TC4 and CDC25 are indicated to have utility, in systemic or topical therapy, to treat a wide variety of cytoproliferative conditions, including malignancy. While it is preferred to administer TC4 and CDC25 together, especially as a complex, either may be administered alone to treat cytoproliferative disease. TC4 has been suggested to play a role in mitosis (26). However, since TC4 has heretofore been known as a nuclear protein (26), its use in inhibiting epidermal growth factor is surprising.

Several types of delivery systems and carriers are contemplated. There are no limitations on the nature of acceptable carrier so long as they are efficacious for their intended use and cannot degrade the activity of the epidermal growth factor inhibitor.

The first embodiment is topically for the elimination of conditions such as psoriasis, keloid scars, warts and keratoses. For topical application, epidermal growth factor inhibitor can be included in various pharmaceutically acceptable carriers and/or adjuvants such as ointments, lotions, salves or creams, preferably in combination with purified collagen. Epidermal growth factor inhibitor may also be impregnated into transdermal patches, plasters, and bandages, preferably in a liquid or semi-liquid form. Epidermal growth factor inhibitor also can be delivered in aqueous solution for injection directly into the afflicted area.

Another application is systemically for the reduction of existing tumors and the prophylaxis and inhibition of new tumor growth such as carcinomas, sarcomas, tumors of the hematopoietic system, germ cell tumors and benign proliferations of these same cell types regardless of the organ of origin. When administered systemically, epidermal growth factor inhibitor may be formulated into liquids, tablets, pills and the like for enteral administration or in liquid form for injection.

Another application is for treatment of disorders of the mucous membranes of the body, including the upper respiratory system, the mouth and pharynx, the external coverings of the eye, the lower female genital tract and the anus. Such disorders include leukoplakia and leukoplakia vulvae. Epidermal growth factor inhibitor can be formulated in mouthwashes, rinses, sprays, creams, ointments and salves, designed to be used in affected mucous membranes.

The Epidermal Growth Factor Inhibitor of this invention is also usefully combined in compositions containing antiviral components, such as adenine arabinoside and/or antineoplastic components, such as adriamycin or cytoxan and/or antimicrobial agents, e.g. antibiotics and the like.

It should be appreciated that the specification depicts presently preferred embodiments of the invention. Other changes and modifications may be made, as would be apparent to those skilled in the art, without departing from the spirit and scope of the invention.

REFERENCES

1. Laurence, D. J. R., Gusterson, B. A.: The epidermal growth factor. *Tumor Biol.*, 1990, 11:229–261.
2. Coleman, S., Silberstein, G. B., Daniel, C. W.: Ductal morphogenesis in the mouse mammary gland: evidence supporting a role for epidermal growth factor. *Dev. Biol.,* 1988, 127:304–315.
3. Taub, M., Wang, Y., Szcaesny, T. M., Kleinman, H. K.: Epidermal growth factor or transforming growth factor a is required for kidney tubulogenesis in matrigel cultures in serum-free medium, 1990, *Proc. Natl. Acad. Sci.* (U.S.A.), 87:4002–4006.
4. Greenfield, C., Hiles, I., Waterfield, M. D., Federwisch, M., Wollmer, A., Blundell, T. L., McDonald, N.: Epidermal growth factor binding induces a conformational change in the external domain of its receptor. 1989, *EMBO J., B:*4115–4123.
5. Nickoloff, B. J., Mitra, R. S.: Inhibition of $^{125}$I-epidermal growth factor binding to cultured keratinocytes by antiproliferative molecules gamma interferon, cyclosporin A, and transforming growth factor-beta. 1989, *J. Invest. Dermatol.* 93:799–803.
6. Imamoto, A., L. M. Beltran, J. DiGiovanni: Differential mechanism for the inhibition of epidermal growth factor binding to its receptor on mouse keratinocytes by anthrones and phorbol esters. 1990, *Carcinogenesis* 11:1543–1549.
7. Hori, T., S. Kashiyama, M. Hayakawa, S. Shimbamoto, M. Tsujimoto, N. Oku, F. Ito: Possible role of prostaglandins as negative regulators in growth stimulation by tumor necrosis factor and epidermal growth factor in human fibroblasts. 1989, *J. Cell. Physiol.* 141:275–280.
8. Murthy, U., D. J. Rieman, U. Rodeck: Inhibition of TGF alpha-induced second messengers by anti-EGF receptor antibody-425. 1990, *Biochem. Biphys. Res. Comm.* 172:471–476.
9. Rodeck, U., N. Williams, U. Murthy, M. Herlyn: Monoclonal antibody 425 inhibits growth stimulation of carcinoma cells by exogenous EGF and tumor-derived EGF-TGF-alpha. 1990, *J. Cell. Biochem.* 44:69–79.
10. Ennis, B. W., E. M. Valverius, S. E. Bates, M. E. Lippman, F. Bellot, R. Kris, J. Schlessinger, H. Masui, A. Goldenberg, J. Mendelsohn, R. B. Dickson: Anti-epidermal growth factor receptor antibodies inhibit the autocrine-stimulated growth of MDA-468 human breast cancer cells. 1989, *Molec. Endocrinol.* 3:1830–1838.
11. Elizalde, P. V., E. H. Charreau: Alpha-transforming growth factorlike activities and bifunctional regulators of cell growth in human malignant neoplasms. 1990, *Cancer Investig.* 8:365–374.
12. Matsunami, R. K., Campion, S. R., Niyogi, S. K., Stevens, A.: Analogs of human epidermal growth factor which partially inhibit the growth factor-dependent protein-tyrosine kinase activity of the epidermal growth factor receptor. 1990, *FEBS Letters* 264:105–108.
13. Eppstein, D. A., Marsh, Y. V., Schryver, B. B., Bertics, P. J.: Inhibition of epidermal growth factor/transforming growth factor-α-stimulated cell growth by a synthetic peptide. 1989, *J. Cell. Physiol.* 141:420–430.
14. Strayer, D. S., Leibowitz, J. L.: Inhibition of epidermal growth factor-induced cellular proliferation. 1987, *Am. J. Pathol.* 128:203–209.
15. Strayer, D. S., Skaletsky, E., Cabirac, G., Sharp, P. A., Corbeil, L. B., Sell, S., Leibowitz, J. L.: Malignant rabbit fibroma virus causes secondary immunosuppression in rabbits. 1983. *J. Immunol.* 130:399–404.
16. Twardzik, D. R., Brown, J. P., Ranchalis, J. E., Todaro, G. J., Moss, B.: Vaccinia virus-infected cells release a novel polypeptide functionally related to transforming and epidermal growth factors. 1985, *Proc. Natl . Acad. sci.* (USA), 82:5300–5304.
17. Stroobant, P., Rice, A. P., Gullick, W. J., Cheng, D. J., Kerr, I. M., Waterfield, M. D.: Purification and characterization of vaccinia virus growth factor. 1985, *Cell,* 42:383–393.
18. Towbin, H, Staheiln, T, Gordon, J.: Electrophoretic transfer of proteins from polyacrylamide gels to nitrocellulose sheets: Procedure and some applications. 1979, *Proc. Natl. Acad. Sci.* (U.S.A.) 76:4350–4354.
19. Matsudaira, P.: Sequence from picomole quantities of proteins electroblotted onto polyvinylidene difluoide membranes. 1987, *J. Biol. Chem.,* 261:10035–10038.
20. Pearson, W. R., Lipman, D. J.: Improved tools for biological sequence comparison. 1988, *Proc. Natl. Acad. Sci.* (U.S.A.), 85:2444–2448.
21. Drivas, G. T., Shih, A., Coutavas, E., Rush, M. G., D'Eustachio, P.: Characterization of four novel ras-like genes expressed in a human teratocarcinoma cell line. 1990, *Mol. Cell. Biol.,* 10:1793–1798.
22. Bischoff, F. R., Ponstingl, H.: Catalysis of guanine nucleotide exchange on Ran by the mitotic regulator RCC1. 1991, *Nature,* 354:80–82.
23. Downward, J., Parker, P., Waterfield, M. D.: Autophosphorylation sites on the epidermal growth factor receptor. 1984, *Nature,* 311:483–485.
24. Ahn, N. G., J. E. Weiel, C. P. Chan, E. G. Krebs: Identification of multiple epidermal growth factor-stimulated protein serine/theonine kinases from Swiss 3T3 cells. 1990, *J. Biol. Chem.* 265:11487–11494.
25. Ahn, N. G., E. G. Krebs: Evidence for an epidermal growth factor-stimulated protein kinase cascade in Swiss 3T3 cells. 1990, *J. Biol. Chem.* 265:11495–11501.
26. Costavas, E., et al.: Characterization of proteins that interact with the cell-cycle regulatory protein Ran/TC4. 1993, *Nature.* 366:585–587.

What is claimed is:

1. An isolated, purified epidermal growth factor inhibitor protein which inhibits epidermal growth factor-induced cellular proliferation, said isolated, purified epidermal growth factor protein being recovered from rabbit kidney cells infected with a malignant rabbit fibroma virus.

2. An isolated, purified epidermal growth factor inhibitor protein from a rabbit comprising:

a first segment having a sequence HLTGEFEKKTS (SEQ ID NO: 1); and a second segment having a sequence KLIGDPNLEFVAMPALAPPEVVMDPALAAQYEHDLEV (SEQ ID NO: 2), connected to the first segment by at least one peptide bond.

3. An isolated, purified epidermal growth factor inhibitor protein from a rabbit wherein the protein comprises a segment having a sequence LMDQNLKAALNAEG (SEQ ID NO: 3).

4. An isolated, purified rabbit epidermal growth factor inhibitor protein or a fragment of the isolated, purified rabbit epidermal growth factor inhibitor protein having the epidermal growth factor inhibitory activity comprising a string of amino acids as set forth in SEQ ID NO: 1, SEQ ID NO: 2, or SEQ ID NO: 3.

* * * * *